US010828126B2

(12) United States Patent
Bayer et al.

(10) Patent No.: US 10,828,126 B2
(45) Date of Patent: Nov. 10, 2020

(54) X-RAY MARKER FOR ABSORBABLE METALLIC SCAFFOLDS HAVING HIGH X-RAY VISIBILITY AND INTEGRATED SELF-PASSIVATION EFFECT

(71) Applicant: CORTRONIK GmbH, Rostock (DE)

(72) Inventors: Ullrich Bayer, Bad Doberan (DE); Daniel Lootz, Andelfingen (CH); Niels Grabow, Rostock (DE); Sabine Illner, Rostock (DE); Thomas Eickner, Rostock (DE); Klaus-Peter Schmitz, Warnemuende (DE)

(73) Assignee: CORTRONIK GmbH, Rostock-Warnemuende (DE)

( * ) Notice: Subject to any disclaimer, the term of this patent is extended or adjusted under 35 U.S.C. 154(b) by 544 days.

(21) Appl. No.: 15/665,959

(22) Filed: Aug. 1, 2017

(65) Prior Publication Data
US 2018/0042693 A1    Feb. 15, 2018

(30) Foreign Application Priority Data

Aug. 11, 2016    (DE) .................. 10 2016 114 894

(51) Int. Cl.
| A61L 31/02 | (2006.01) |
| A61L 31/10 | (2006.01) |
| A61B 90/00 | (2016.01) |
| A61L 31/14 | (2006.01) |
| A61L 31/18 | (2006.01) |
| A61B 17/00 | (2006.01) |

(52) U.S. Cl.
CPC ............ *A61B 90/39* (2016.02); *A61L 31/022* (2013.01); *A61L 31/10* (2013.01); *A61L 31/145* (2013.01);
(Continued)

(58) Field of Classification Search
CPC .. A61L 31/022; A61L 31/148; A61L 2400/16; A61L 2420/08; A61L 2420/04;
(Continued)

(56) References Cited

U.S. PATENT DOCUMENTS 6,129,754 A * 10/2000 Kanesaka ............... A61F 2/856
606/153
6,355,058 B1 * 3/2002 Pacetti .................... A61L 29/18
427/2.25
(Continued)

FOREIGN PATENT DOCUMENTS

| EP | 2399619 A2 | 12/2011 |
| EP | 2457601 A2 | 5/2012 |
| EP | 3165238 A1 | 10/2017 |

OTHER PUBLICATIONS

Proikakis et al, "Swelling and hydrolytic degradation of poly(D,L-lactic acid) in aqueous solutions", (2006), Polymer Degradation and Stability, vol. 91, pp. 614-619. (Year: 2006).*
(Continued)

*Primary Examiner* — Paul B Prebilic
(74) *Attorney, Agent, or Firm* — Greer, Burns & Crain, Ltd.; Steven P. Fallon (57) ABSTRACT

A medical implant that includes a scaffold having at least one receptacle for an X-ray marker. The scaffold includes a first metal. At least one (preferably monolithic) X-ray marker is disposed in the receptacle. The X-ray marker includes a second metal. An electrically insulating coating is upon the X-ray marker to prevent corrosion-promoting contact between the X-ray marker and the scaffold.

18 Claims, 5 Drawing Sheets

(52) U.S. Cl.
CPC ............. *A61L 31/148* (2013.01); *A61L 31/18* (2013.01); *A61B 2017/00898* (2013.01); *A61B 2017/00929* (2013.01); *A61B 2090/3966* (2016.02); *A61B 2090/3991* (2016.02)

(58) Field of Classification Search
CPC .. A61B 90/39–2090/3916; A61B 2017/00898; A61B 2017/00929; A61B 2560/04; A61B 2560/0443; A61B 2560/0456; A61B 2576/02
USPC ........................................................ 623/1.34
See application file for complete search history.

(56) References Cited

U.S. PATENT DOCUMENTS

| | | | |
|---|---|---|---|
| 8,377,112 B2* | 2/2013 | Griffin | A61B 17/12022 606/200 |
| 2002/0103528 A1* | 8/2002 | Schaldach | A61F 2/86 623/1.15 |
| 2002/0193867 A1* | 12/2002 | Gladdish, Jr. | A61F 2/91 623/1.15 |
| 2007/0043429 A1* | 2/2007 | Hegel | A61F 2/82 623/1.15 |
| 2011/0319982 A1* | 12/2011 | Bayer | A61L 31/022 623/1.34 |
| 2013/0197626 A1* | 8/2013 | Thompson | A61L 31/16 623/1.34 |

OTHER PUBLICATIONS

Wolfram Lamers, European Search Report for Application No. 17180933.8, dated Dec. 20, 2017.

Mambaye N'diaye et al: "Water Absorption of Poly(methyl methacrylate) Measured by Vertical Interference Microscopy", Langmuir, (Jul. 27, 2012), pp. 11609-11614.

* cited by examiner

X-RAY MARKER FOR ABSORBABLE METALLIC SCAFFOLDS HAVING HIGH X-RAY VISIBILITY AND INTEGRATED SELF-PASSIVATION EFFECT

PRIORITY CLAIM

This application claims priority under 35 U.S.C. § 119 and all applicable statutes and treaties from prior German Application DE 10 2016 114 894.6, filed Aug. 11, 2016.

FIELD OF THE INVENTION

A field of the invention relates to medical implants. An example implant is a stent, which includes a scaffold, and in particular a stent scaffold, which has a degradable design, which dissolves in the patient's body in a defined manner following implantation during a certain time period.

BACKGROUND

Such implants are generally equipped with one or more X-ray markers. The X-ray markers permit a position determination of the implant via X-ray imaging during and after an implantation procedure.

Figure 1:
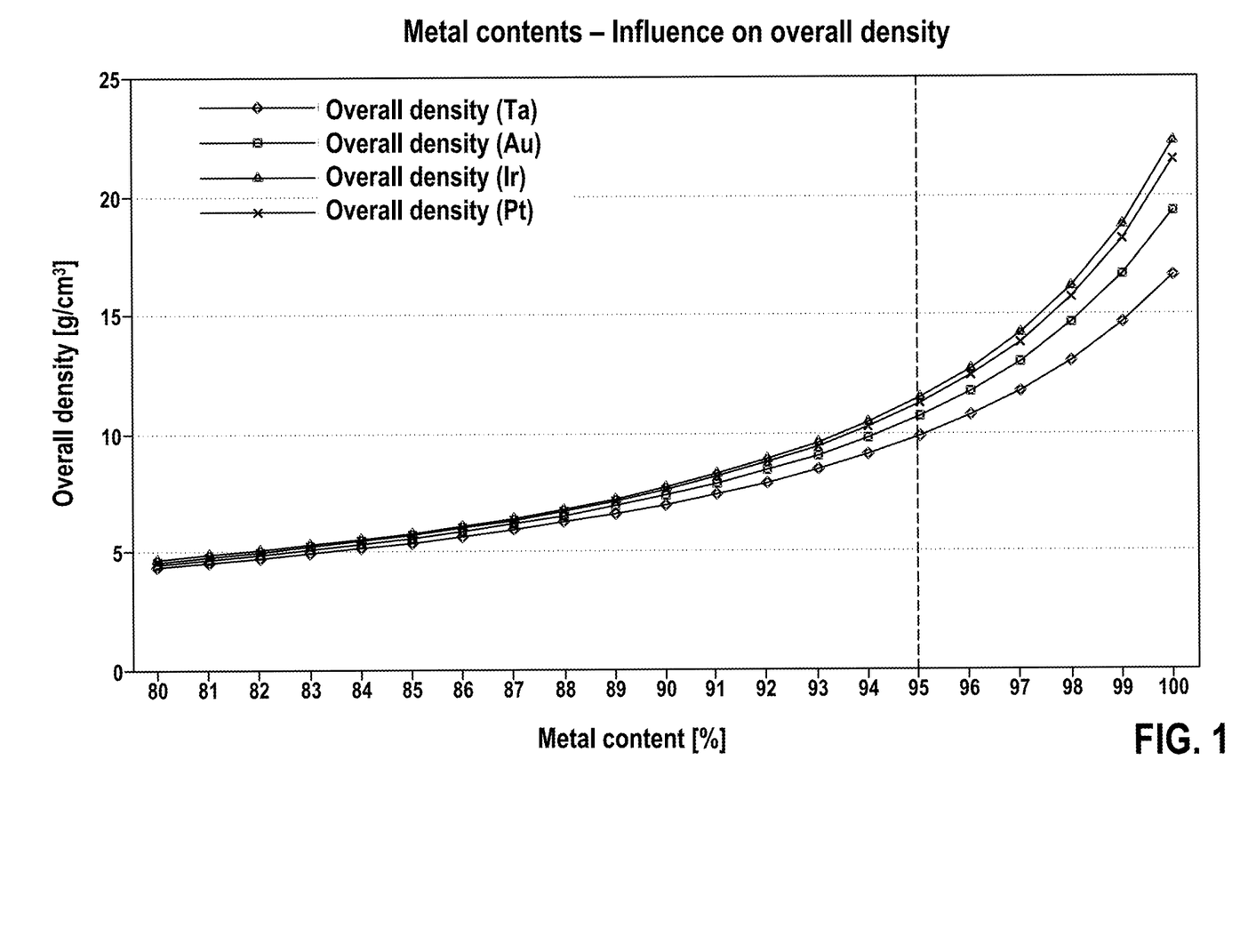
FIG. 1 shows an illustration of the composite density resulting as a function of the metal content. The vertical line represents the maximum metal content that is technologically producible at present as a composite.

Composite X-ray markers, such as those described in EP 2 457 601, are material combinations of metallic marker particles and polymeric adhesives. The percent by weight of X-ray absorbing particles in the composite decisively determines the X-ray visibility. The proportion thereof, however, cannot be significantly higher than 90 wt. %. At higher proportions, the mixture is already so highly viscous in the uncured state that processing, such as injection into receptacles, known as eyelets, of the scaffold, is no longer possible. Due to the differences in density between polymeric adhesives (Rho<2 g/cm$^3$) and X-ray absorbing metals such as Ta (Rho>16 g/cm$^3$) the volume ratios behave exactly contrary to the respective mass ratios, further optimization of this technology is difficult. Even if attempts to introduce 95 wt. % of X-ray absorbing particles into a polymer-containing composite, and also to introduce this in a defined manner into an eyelet, were to be successful, it would nonetheless only be possible to use half of the particular X-ray absorption potential, due to the density of the composite that arises, as shown in FIG. 1. Especially with respect to the implementation of lower wall thicknesses, this results in reduced, no longer relevant X-ray visibility.

Figure 2A:
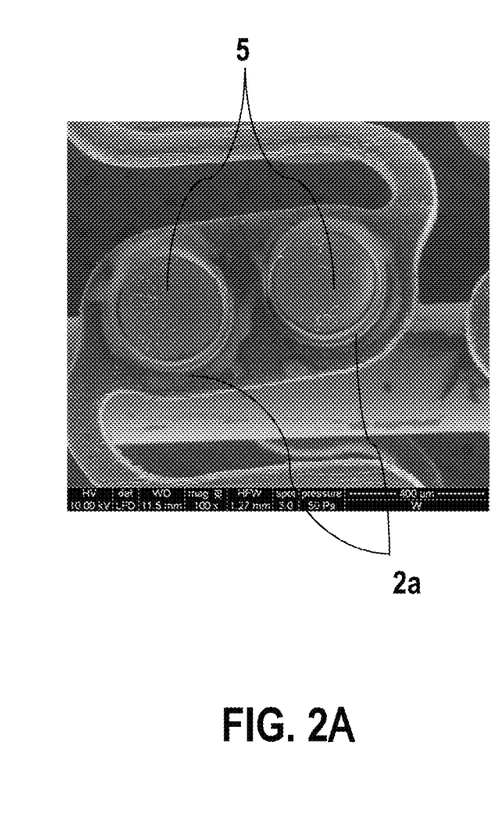
FIGS. 2A-2B shows a glued-in solid marker having an unevenly filled adhesive gap.
Figure 2B:
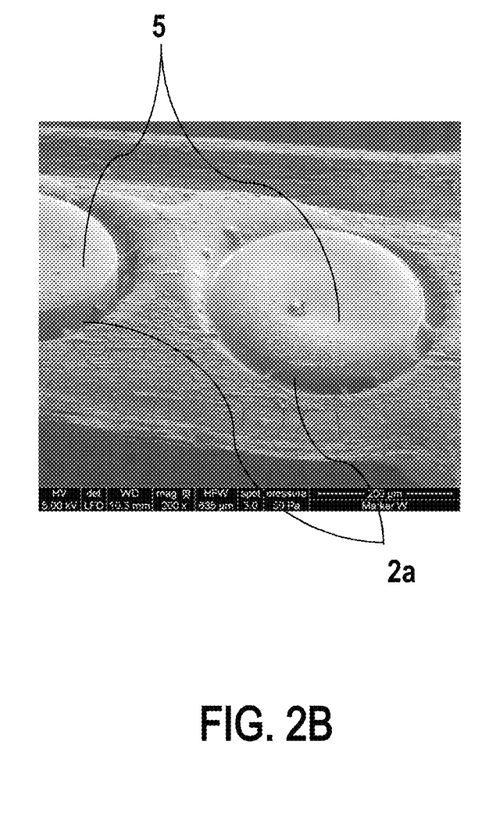

Another known approach adhesively bonds solid markers in the eyelets of absorbable scaffolds. Such adhesive bonding can cause undesirable accelerated corrosion in the marker area, as is shown in FIGS. 2A-2B, for example. The adhesive gap 2a (approximately 20 micrometers) of a silicone adhesive that is used cannot be evenly distributed across the circumference for technological reasons. After the scaffold has been introduced into the patient, dilated and spent a residence time of several days to weeks in the vascular environment, degradation effects cause a shift of the X-ray marker 5 in the respective eyelet. This results at least in punctiform, and also extensive, metallic direct contact between the marker 5 and the surrounding bulk material of the scaffold. Locally increased, rapidly progressing corrosion of the marker environment ensues. It is essential to avoid this effect.

Another approach, such as in EP 2 399 619, encases a solid X-ray marker with foreign metals to reduce the risk of corrosion. While the risk of local element formation or corrosion is considerably reduced in these variants, the technological manufacturing complexity is very high.

X-ray markers introduced into the eyelets of polymeric scaffolds by way of form fit and force fit method are described in Bayer et al, U.S. Pat. No. 10,272,183. Gaps between the marker and the scaffold are subsequently filled using a polymeric material. Polymer scaffolds have mechanical properties that are not as advantageous as metal scaffolds. Degradable polymers are bulk or surface eroding, and water attacks chemical bonds converting long polymer chains into shorter water-soluble fragments. This causes a reduction in molecular weight without the loss of physical properties as the polymer is still held together by the crystalline regions. Water penetrates the device leading to metabolization of the fragments and bulk erosion. Surface erosion of the polymer occurs when the rate at which the water penetrating the device is slower than the rate of conversion of the polymer into water-soluble materials.

SUMMARY OF THE INVENTION

The invention relates to a medical implant and a corresponding method for producing the implant which considerably lowers the risk of corrosion due to a cooperation of the scaffold with the X-ray marker, in particular in an aqueous environment.

A preferred embodiment provides a medical implant that includes a scaffold having at least one receptacle for an X-ray marker. The scaffold includes a first metal. At least one (preferably monolithic) X-ray marker is disposed in the receptacle. The X-ray marker includes a second metal. An electrically insulating coating is upon the X-ray marker to prevent corrosion-promoting contact between the X-ray marker and the scaffold.

The X-ray marker preferably has a monolithic design, specifically a contiguous base body and, in this case, is not composed of a plurality of marker particles held together by way of a separate adhesive.

BRIEF DESCRIPTION OF THE DRAWINGS

Further features and advantages of the present will be described in the description of exemplary embodiments of the invention, based on the drawings. In the drawings.

DETAILED DESCRIPTION OF THE PREFERRED EMBODIMENTS

A preferred embodiment implant includes a scaffold that is preferably a stent scaffold, which is configured to be implanted into a blood vessel of a patient. The stent scaffold includes a plurality of mutually connected struts, which form the cells of the stent scaffold. The stent scaffold has two ends, which surround an inlet opening and an outlet opening of the stent scaffold through which blood can flow into, and back out of, an inner chamber of the stent scaffold surrounded by the stent scaffold. A receptacle is preferably in the form of a through-passage in a strut of the scaffold or stent scaffold, which is preferably disposed at one of the ends. Two adjoining receptacles are preferably provided on such a strut, which are each designed as through-passages and into which a respective X-ray marker is introduced. Preferably, two such adjoining receptacles, which are also referred to as eyelets, are provided at the two ends of the stent scaffold. In this way, it is possible to ascertain the exact spatial location and position of the stent by way of the X-ray markers, which are configured to create a clear contrast in an X-ray image. According to the invention, an eyelet can take on any shape that is required for the corresponding application, for example round, oval, trapezoidal or square. In particular, the eyelet has a size of 10 to 1000 μm, of 10 to 100 μm, and of 20 to 200 μm.

According to one embodiment of the implant according to the invention, the coating is formed from swellable material (s) such that it undergoes an increase in volume upon contact with a medium containing water and spaces the X-ray marker with respect to the scaffold to avoid the contact.

Furthermore, according to one embodiment of the implant according to the invention, it is provided that the X-ray marker has a surface having a pore structure, wherein the pore diameter is preferably in the range of 0.5 micrometers to 3 micrometers, or that the core has a surface structure that preferably has a surface roughness value Ra in the range of 0.5 micrometers to 3 micrometers.

Furthermore, according to one embodiment of the implant according to the invention, it is provided the surface is oxidized by way of plasmachemical treatment, or treated mechanically by micro-peening, to produce the pore structure.

Furthermore, according to one embodiment of the implant according to the invention, it is provided that the coating is received in the pores or in the surface structure and designed to emerge from the pores or the surface structure upon contact with a medium containing water, so that preferably centering of the X-ray marker in the receptacle takes place, and in particular that self-passivation of the X-ray marker takes place.

Furthermore, according to one embodiment of the implant according to the invention, it is provided that the X-ray marker is adhesively attached in the receptacle. A separate adhesive can be used for this purpose, or the coating itself forms the required adhesive.

Furthermore, according to one embodiment of the implant according to the invention, it is provided that the second metal is one of the following metals: tungsten, tantalum, gold, platinum, iridium.

Furthermore, according to one embodiment of the implant according to the invention, it is provided that the scaffold is a degradable scaffold, which is designed to completely dissolve within a predefined time period after having been implanted into a human or animal body.

Furthermore, according to one embodiment of the implant according to the invention, it is provided that the first metal is magnesium, wherein the magnesium is a component of a magnesium alloy which the scaffold includes or of which the scaffold is made.

Furthermore, according to one embodiment of the implant according to the invention, it is provided that the coating includes one or more of the following substances: a polymer, and in particular a swellable, insoluble, cross-linked polymer, such as, among other things, polyacrylates, polyacrylic acid (PAA), polylauric acid vinyl ester, polyvinylimidazole, polyvinylpyrrolidone, polyglycolic acid (PGA), polyethylene glycol (PEG), hyaluronic acid (HA), polyureas, polyurethanes, water glass, cyanoacrylate, paraffin in combination with a suitable cross-linking agent and, if necessary, a suitable solvent.

A method for producing a medical implant provides a scaffold which includes at least one receptacle for an X-ray marker, wherein the scaffold includes a first metal, and wherein an X-ray marker comprising a second metal is provided, to which an electrically insulating coating is applied, and wherein the coated X-ray marker is adhesively attached in the receptacle.

According to one embodiment of the method according to the invention, it is provided that the X-ray marker is provided with a pore structure or surface structure by way of treatment of the surface of the X-ray marker.

Furthermore, according to one embodiment of the implant according to the invention, it is provided that the X-ray marker is brought in contact with a coating solution for applying the coating.

Furthermore, according to one embodiment of the implant according to the invention, it is provided that this coating solution includes a hydrogel monomer, a cross-linking agent, a polymerization initiator and a polymerization catalyst.

According to one embodiment of the invention, monomers such as acrylates, lauric acid vinyl esters, vinylimidazole, vinylpyrrolidone, diisocyanates and the like can be used as the hydrogel monomer, vinylogous monomers being preferred. Furthermore, according to one embodiment of the invention, cross-linking agents in the form of N,N'-methylenebis(acrylamide) (MBAA), glutardialdehyde, 1-ethyl-3-(3-dimethylaminopropyl)carbodiimide/N-hydroxysuccinimide (EDC/NHS) or others may be used.

Furthermore, according to one embodiment, tetramethylenediamine (TEMED) may be used as a polymerization catalyst.

Furthermore, according to one embodiment, ammonium persulfate (APS) or azobis(isobutyronitrole) (AIBN) may be used as polymerization initiators.

According to one embodiment, it is furthermore provided that the polymerization on the surface of the X-ray marker can be thermally or photochemically activated.

Furthermore, according to one embodiment, the polymerization process may be catalytically supported in a supplementary manner, such as by way of an appropriate composition of the surface of the X-ray marker, which can be formed, for example, by an amorphous oxide layer (such as $WO_3$ or sodium tungstate as a layer component).

According to one embodiment, it is furthermore preferably provided that the coated X-ray marker is glued into the associated receptacle of the scaffold. For example, an adhesive comprising silicone can be used as the adhesive for this purpose.

Furthermore, according to an alternative embodiment of the implant according to the invention, it is provided that the coating solution includes a swellable polymer, wherein the coating solution, in particular, furthermore includes an adhesive.

According to one embodiment, the coating solution can include a polymer or a dissolved superabsorbent polymer, such as polyacrylic acid (PAA), polyglycolic acid (PGA), polyethylene glycol (PEG), hyaluronic acid (HA), or other such substances. Furthermore, in addition to one or more of these or other suitable polymers, the coating solution can include ELA-NCO or water glass or a cyanoacrylate, or diluted aqueous or solvent-containing mixtures (such as a chloroform-containing paraffin solution). Paraffin or water glass are advantageously electrically insulating and inert.

According to one embodiment of the invention, the coating solution including the swellable polymer is also used as the adhesive, which is to say, according to one embodiment, the X-ray marker is also directly adhesively bonded to the receptacle by way of the coating solution, without the addition of a (silicone) adhesive.

Furthermore, according to one embodiment of the implant according to the invention, it is provided that the X-ray marker is adhesively attached in the receptacle, wherein an adhesive used for this purpose is preferably formed by the coating or the coating solution.

In general, the resulting swellable polymer gel (hydrogel) or the swellable adhesive substitute are preferably biocompatible and swell in the presence of aqueous (including chloride-containing) solutions or blood.

As a result of the swellable, electrically insulating coating, preferred embodiments of the invention enable the use of solid X-ray markers (monolithic X-ray markers), the use of which in degradable scaffold materials, such as magnesium alloys, in the past has prompted increased corrosion rates and, resulting therefrom, a considerably shorter service life. The risk of the inadvertently and suddenly occurring formation of local elements during the clinically relevant support period, and the unpredictable corrosion resulting therefrom, along with intensified local hydrogen formation and the associated potential undesirable biological reactions, no longer occurs or is considerably suppressed.

The preferred swelling effect according to the invention causes a considerable increase in volume of the coating, as a consequence of which the polymer/hydrogel emerges from the porous or structured surface of the X-ray marker.

When the polymer impinges upon the wall of the at least one receptacle or eyelet, the swelling effect is diverted in different directions, and additionally the X-ray marker becomes self-centered in the receptacle in the adhesive gap (for example, approximately 20 μm), preventing metal-on-metal contact between the first and the second metals. The corrosive environment itself thus, in particular, causes self-passivation. The degradation progression until the scaffold has been fully converted into the corrosion products thereof is not interrupted.

The invention ultimately allows the marker installation process to be simplified since an increase in the manufacturing tolerances is possible. The subsequent swelling, in particular, prompts self-centering of the X-ray marker, whereby even incompletely centered X-ray markers are acceptable.

Figure 4:
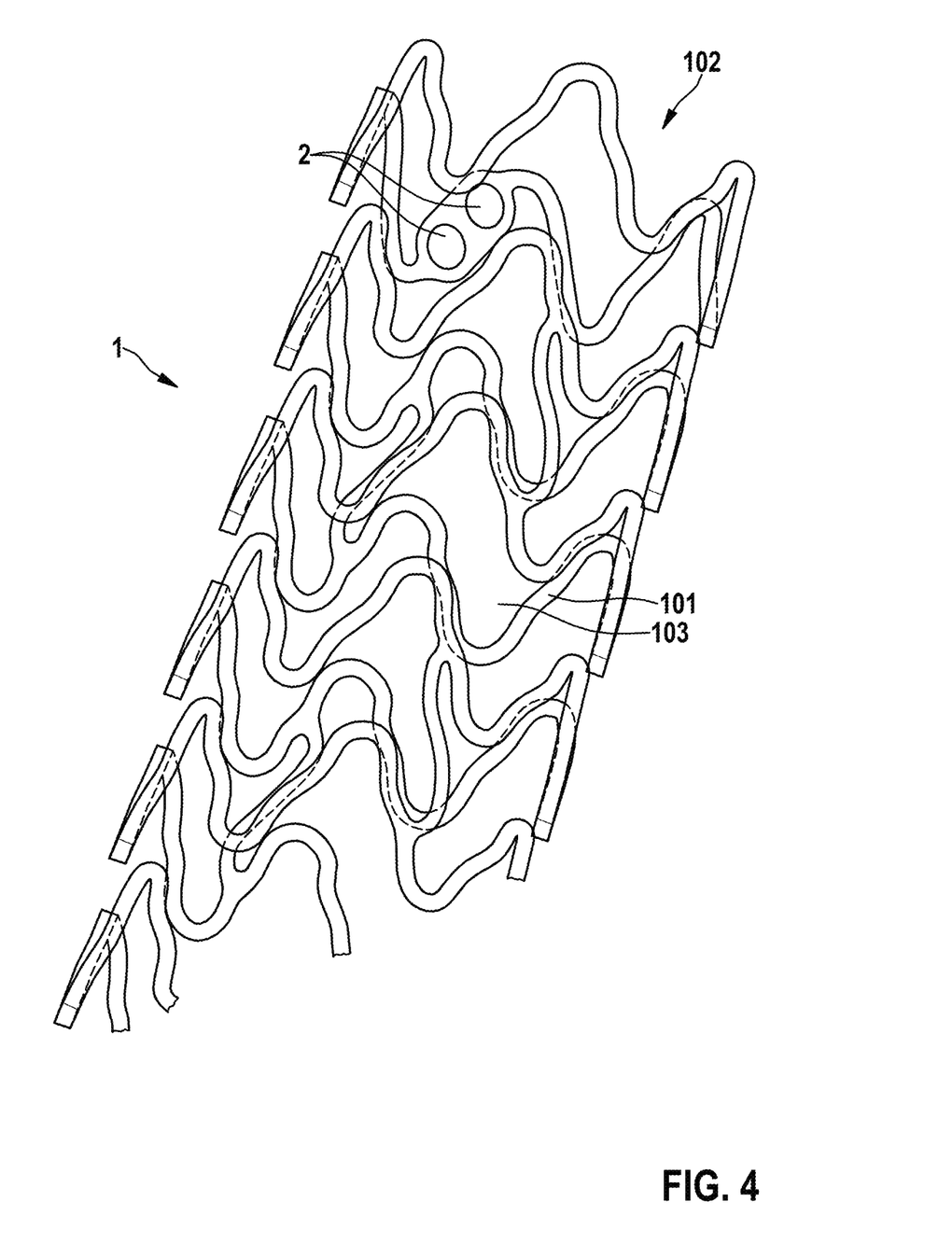
FIG. 4 shows a view of an implant according to the invention comprising adjoining receptacles (eyelets) for X-ray markers.
Figure 5:
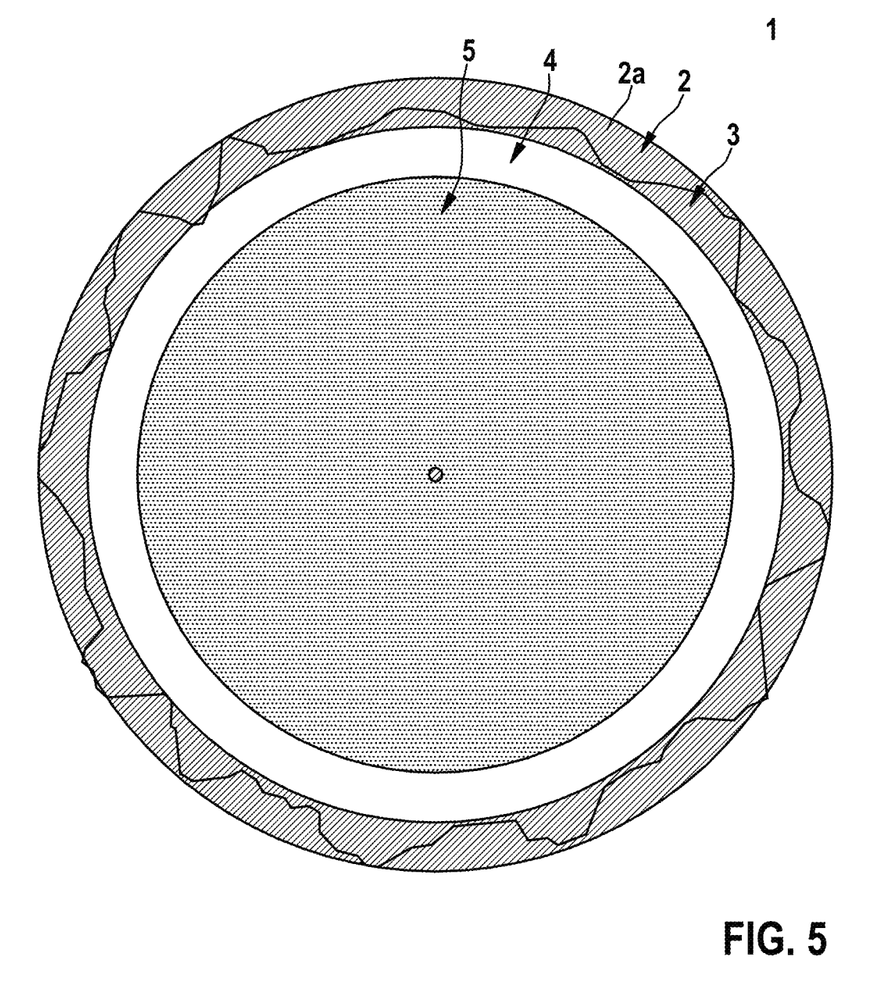
FIG. 5 shows a schematic view of an eyelet according to the invention.

FIG. 4, in connection with FIG. 5, shows a medical implant according to the invention, comprising a scaffold 1, which includes at least one receptacle 2 for an X-ray marker 5.

In particular according to FIG. 4, the scaffold 1 is a stent scaffold, which is configured and provided, for example, to be implanted into a blood vessel of a patient. The stent scaffold 1 includes a plurality of mutually connected struts 101, which form the cells of the stent scaffold 1. The stent scaffold has two ends 102 (only one end is shown in FIG. 4), which surround an inlet opening and an outlet opening of the stent scaffold 1 through which blood can flow into, and back out of, an inner chamber 103 of the stent scaffold 1 surrounded by the stent scaffold 1. The at least one receptacle 2 is preferably designed as a through-passage of a strut 101 of the scaffold or stent scaffold 1. According to FIG. 4, for example, two adjoining receptacles 2 or eyelets 2 are provided at one of the ends 102, or at both ends 102.

When the X-ray markers 5 are disposed in the respective receptacle 2, a peripheral adhesive gap 2a is defined, which is schematically shown in FIG. 5.

The scaffold 1 includes a first metal, preferably magnesium, which is present in the form of a magnesium alloy forming the scaffold 1 and having a composition, for example, of WE43 (a magnesium alloy comprising yttrium and other rare earth elements) or a composition comprising aluminum and optional zinc as alloying elements, and at least one X-ray marker 5 disposed in the receptacle 2. The at least one X-ray marker 5, or the multiple markers 5, disposed in the respective receptacle 2 furthermore include a second metal, which may be one of the metals described herein (see above and exemplary embodiments hereafter).

A magnesium alloy in the present example shall be understood to mean a metal structure, the main component of which is magnesium. The main component is the alloying component having the highest percentage by weight in the alloy. A content of the main component is preferably more than 50 wt. %, in particular more than 70 wt. %, and especially particularly preferably more than 90 wt. %. The biocorrodible magnesium alloy of the core preferably includes yttrium and further rare earth metals, since such an alloy stands out with its physicochemical properties and high compatibility, in particular also the decomposition products thereof. In the present example, the collective term "rare earth metals" shall include scandium (21), yttrium (39), lanthanum (57) and the 14 elements following lanthanum (57), which is to say cerium (58), praseodymium (59), neodymium (60), promethium (61), samarium (62), europium (63), gadolinium (64), terbium (65), dysprosium (66), holmium (67), erbium (68), thulium (69), ytterbium (70) and lutetium (71). A person skilled in the art is familiar with a plurality of magnesium alloys. A particularly preferred magnesium alloy has a composition of 5.2 to 9.9 wt. % rare earth metals, of which yttrium is 3.7 to 5.5 wt. %, and the remainder is <1 wt. %, wherein magnesium accounts for the content in the alloy that is missing to make up 100 wt. %. In particular, a preferred magnesium alloy has a composition of 3.7 to 5.5 wt. % yttrium, 1.5 to 3 wt. % neodymium, 0.3 to 1 wt. % zirconium, 0.4 to 0.55 wt. % gadolinium, 0.4 to 0.55 wt. % dysprosium, <0.006 iron, and the remainder being <1 wt. %, wherein magnesium accounts for the content in the alloy that is missing to make up 100 wt. %. Furthermore, alloys based on magnesium in the form of Mg—Zn—Al, Mg—Zn—Ca, Mg—Zn or Mg—Al are preferred, wherein these alloys at the most include traces of rare earth metals or further elements. A preferred magnesium alloy has a composition of 1.5 to 7.0 wt. % zinc and 0.5 to 10.0 wt. % aluminum, the remainder being <0.0063 wt. %, wherein magnesium accounts for the content in the alloy that is missing to make up 100 wt. %. Furthermore, a preferred magnesium alloy has a composition of 3.0 to 7.0 wt. % zinc and 0.001 to 0.6 wt. % calcium, the remainder being <0.0048 wt. %, wherein magnesium accounts for the content in the alloy that is missing to make up 100 wt. %. Furthermore, a preferred magnesium alloy has a composition of 1.0 to 10.0 wt. % aluminum, the remainder being <0.0048 wt. %, wherein magnesium accounts for the content in the alloy that is missing to make up 100 wt. %.

According to the invention, so as to prevent the corrosion-promoting contact between the second metal of the at least one X-ray marker 5 and the first metal (or further metals) of the scaffold 1, the at least one X-ray marker 5 includes an electrically insulating coating 3, which particularly preferably is designed to be swellable so as to undergo an increase in volume upon contact with a medium containing water (in particular, upon contact with blood after implantation).

This swelling upon contact with the medium causes the X-ray marker to become centered in the receptacle and to become appropriately spaced from an edge of the receptacle, resulting in a uniform adhesive gap 2a. The increase in volume furthermore effectively causes self-passivation of the marker 5 upon contact with the aqueous medium. Due to the increase in volume of the coating, the marker is effectively shielded (preventing corrosion).

Figure 3A:
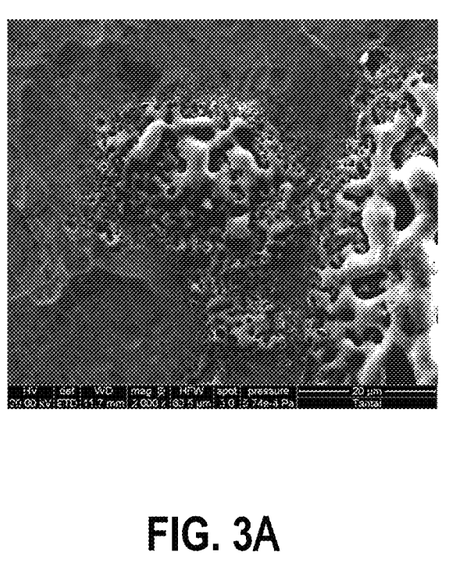
FIG. 3A-3B shows a porous surface of an X-ray marker oxidized by way of plasmachemical treatment, made of tantalum (FIG. 3A) and tungsten (FIG. 3B)
Figure 3B:
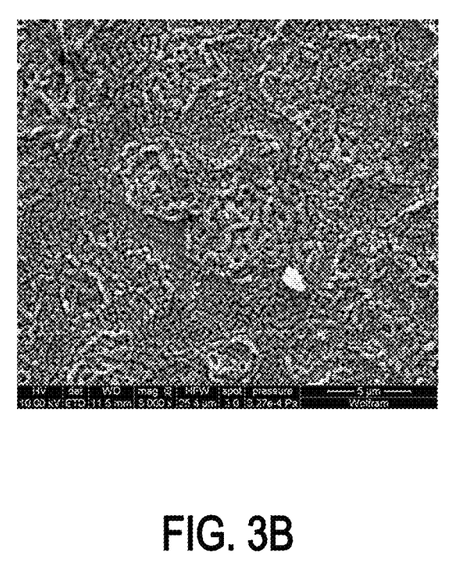

For better adhesion of the coating 3, the surface 4 of the at least one X-ray marker 5 is preferably provided with a surface roughening by producing the solid marker 5 from W (or Ta) and oxidizing the same by way of plasmachemical treatment (see FIGS. 3A-3B), or by designing the same as a precious metal marker 5 (made of Au or Pt), which is treated mechanically by micro-peening The natural crystalline oxide layer already present (a few nm thick) in the case of W and Ta is replaced by an amorphous oxide layer (several μm thick). Tungsten and tantalum markers 5 thus have a pore structure having pore diameters between 0.5 and 3 μm, and the pore depth is, in particular, slightly less than the layer thickness. The precious metal markers 5 furthermore have surface roughness values between Ra 0.5 and 3 μm.

According to a first example of the invention, the markers 5 thus treated, having a diameter of approximately 320 μm, for example, are immersed in a solution to yield the swellable coating.

As a result of the application of a negative pressure of less than 200 mbar, for example using a desiccator, the pores are filled with the swellable polymer, or the monomer solution forming the same by way of polymerization, and the air bubbles are removed. Thereafter, a drying process, polymerization (curing in air or in a thermally activated manner) or immediate adhesive bonding in the respective eyelet 2 takes place.

According to one example of the invention, the solution to yield the swellable coating includes: an additive solution comprising a hydrogel monomer, a cross-linking agent, an initiator and a polymerization catalyst. The hydrogel monomer used is preferably vinylogous monomers, such as lauric acid vinyl ester, vinylimidazole, vinylpyrrolidone and the like. N,N'-methylenebis(acrylamide) (MBAA), glutardialdehyde, 1-ethyl-3-(3-dimethylaminopropyl)carbodiimide/N-hydroxysuccinimide (EDC/NHS) or others, for example, may be used as the cross-linking agent. Ammonium persulfate (APS) or azobis(isobutyronitrole) (AIBN) may be used as initiators, for example. Tetramethylenediamine (TEMED) may be used as a polymerization catalyst, for example. The polymerization process on the marker surface 4 can be thermally or photochemically activated, or it may be catalytically supported by the composition of the amorphous oxide layer (such as $WO_3$ or sodium tungstate as a layer component). Subsequent adhesive bonding of the marker 5 thus insulated in the eyelet 2 takes place, for example, by way of a suitable adhesive.

According to an alternative example, the coating solution can be made of a swellable polymer, which may also be used as the adhesive and, if necessary, replace the same. Within this adhesive gel, a swellable polymer is combined with an adhesive substitute. The adhesive gel can be composed of a dissolved superabsorbent polymer, such as polyacrylic acid (PAA), polyglycolic acid (PGA), polyethylene glycol (PEG), hyaluronic acid (HA), or other suitable polymers, and of polyureas or polyurethanes or water glass or cyanoacrylates or diluted aqueous or solvent-containing mixtures (such as chloroform-containing paraffin solution).

This solution to yield the swellable coating is preferably also used as the adhesive, whereby the respective marker 5, if necessary, can also be directly adhesively bonded in the associated eyelet 2, without the addition of a silicone adhesive.

In general, the resulting swellable polymer gel (hydrogel) or the swellable adhesive substitute are biocompatible and swell in the presence of aqueous (including chloride-containing) solutions or blood.

According to a further example of the invention, a scaffold 1 comprising an X-ray marker 5 made of tungsten was provided (see FIGS. 4 and 5), which includes a macroporous surface 4 made of tungsten oxide generated by way of plasmachemical oxidation.

The scaffold 1 includes a degradable magnesium alloy (see FIG. 4), which at the distal end and at the proximal end 102 includes a respective double eyelet 2 (which is to say two adjoining receptacles in the form of through-passages 2 of a strut 101), intended to be filled with X-ray markers 5. The diameter of an eyelet 2 is approximately 350 μm, for example.

Round solid markers 5 made of tungsten are installed in these eyelets 2. The thickness of these tungsten markers is identical to the wall thickness of the scaffold 1 and is, for example, 100 μm. The diameter is approximately 20 μm less than the eyelet diameter. The tungsten marker 5 was previously oxidized by way of plasmachemical treatment in an electrolyte containing sulfuric acid and phosphoric acid. The oxidation of the chemically stable element tungsten is caused by the locally delimited plasma discharges arising at bath voltages>180 V. Individual plasma discharges systematically pass over the tungsten surface in the process. The surface of the marker 5 is thus provided with a portion surface typical of this procedure, which is predominantly made of $WO_3$. The oxide layer thickness is between 3 and 6 μm. Due to the conversion nature of the plasma discharges, the original outer geometry of the marker 5 is preserved, and the oxide layer, as a result of the material integration with the metallic substrate situated beneath, has high adhesive strength (see FIG. 5). This surface structuring also prompts a considerable enlargement of the real surface by at least a factor of 2.

This ensures high wettability. The marker 5 thus treated is subsequently dipped in a solution to yield the swellable coating, which, for example, can be designed according to one of the above-mentioned examples. To remove the air bubbles present in the porous surface 4, this dipping process takes place in a desiccator to which negative pressure of <200 mbar is applied. After a treatment time between 2 and 5 minutes, the degassing process is completed, and rising air bubbles are no longer visible. The marker surface 4 is wetted with the swellable polymer 3 and removed from the coating solution. If necessary, this is followed by thermally initiated polymerization at >50° C., removal of the solvent in a vacuum drying chamber or direct adhesive bonding in the respective eyelet 2.

After this process, the marker 5 is positioned in the eyelet 2. If necessary, the solution to yield the swellable coating (see above), which was previously used (to coat the respective marker 5), is applied to the eyelet environment. After the respective marker 5 has been positioned in the associated eyelet 2, the final thermal treatment is carried out, which results in polymerization of the coating of the X-ray marker surface and brings about a sufficient retaining force of the marker 5 in the eyelet 2. Thereafter, in particular, the installation of the scaffold 1 in a catheter system takes place.

During the vascular intervention of the scaffold 1, the environment of the X-ray marker 5 comes in contact with blood. Thereupon, a swelling process of the polymeric hydrogel 3 commences. This causes an increase in volume and the hydrogel 3 to emerge from the marker surface 4. This also applies to the cut edges of the marker 5. This self-sealing effect represents an encapsulation of the marker 5 and isolation thereof with respect to the remaining scaffold 1. Moreover, technologically induced shortcomings in the process of the marker positioning are compensated for by subsequent self-centering of the marker 5 in the eyelet 2. In this way, it is ensured that no metal-on-metal contact arises, and local element formation is reliably suppressed and no influence on the further degradation process of the scaffold 1 takes place.

According to a further example of the invention, a scaffold 1 comprising an X-ray marker 5 made of tantalum was provided, which includes a macroporous surface 4 made of tantalum oxides generated by way of plasmachemical oxidation. The scaffold 1 used, made of a degradable magnesium alloy (see FIG. 4), once again, has a double eyelet 2 each at the distal end and at the proximal end 102, the eyelet being intended to be filled with X-ray markers 5. The diameter of an eyelet 2 is approximately 350 µm, for example. Round solid markers 5 made of tantalum are installed in these eyelets 2. The thickness of these tantalum markers 5 is identical to the wall thickness of the scaffold 1 and is, for example, 100 µm. The diameter is approximately 20 µm less than the eyelet diameter. The respective tantalum marker 5 was previously oxidized by way of plasmachemical treatment in an electrolyte containing sulfuric acid and phosphoric acid. The oxidation of the chemically stable element tantalum is caused by the locally delimited plasma discharges arising at bath voltages>180 V. Individual plasma discharges systematically pass over the tantalum surface in the process. The surface of the marker 5 is thus provided with a porous surface 4 typical of this procedure, which is predominantly made of tantalum pentoxide $Ta_2O_5$. The oxide layer thickness is between 3 and 6 µm. Due to the conversion nature of the plasma discharges, the original outer geometry of the marker 5 is preserved, and the oxide layer, as a result of the material integration with the metallic substrate situated beneath, has high adhesive strength (see FIG. 5). This surface structuring 4 also prompts a considerable enlargement of the real surface by at least a factor of 2. This ensures high wettability.

The marker 5 thus treated is subsequently dipped in a coating solution, which can correspond to one of the examples illustrated above. So as to remove the air bubbles present in the porous surface 4, this dipping process, once again, takes place in a desiccator to which negative pressure of <200 mbar is applied. After a treatment time between 2 and 5 minutes, the degassing process is completed, and rising air bubbles are no longer visible. The marker surface 4 is wetted with the swellable polymer 3 and removed from the coating solution. If necessary, this is followed by thermally initiated polymerization at >50° C., removal of the solvent in a vacuum drying chamber or direct adhesive bonding in the respective eyelet 2.

After this process, the marker 5 is positioned in the eyelet 2. If necessary, the identical solution to yield the swellable coating (used previously to coat the respective Ta marker 5), is applied to the eyelet environment. After the respective marker 5 has been positioned in the associated eyelet 2, the final thermal treatment is carried out, which results in polymerization of the coating of the X-ray marker surface and brings about a sufficient retaining force of the marker 5 in the eyelet 2. Thereafter, the installation of the scaffold 1 in the catheter system takes place.

According to a further example of the invention, a scaffold 1 comprising an X-ray marker 5 made of gold (Au) was provided, which includes a macroporous surface 4 roughened by way of micro-peening. This scaffold 1 is, once again, made of a degradable magnesium alloy in accordance with FIG. 4 and has a double eyelet 2 each at the distal end and at the proximal end 102, the eyelet being intended to be filled with X-ray markers 5. The diameter of an eyelet 2 is approximately 350 µm, for example. Round solid markers 5 made of gold are installed in these eyelets 2. The thickness of these gold markers is identical to the wall thickness of the scaffold 1 and is, for example, 100 µm. The diameter is approximately 20 µm less than the eyelet diameter. The gold marker 5 was previously roughened by way of micro-peening using corundum particles. The surface roughness thus achieved is between Ra 0.5 µm and Ra 3.0 µm. The surface of the marker 5 is thus provided with a microrough porous surface 4. This surface structuring also prompts a considerable enlargement of the real surface by at least a factor of 2. This is an essential prerequisite for the high wettability.

The marker thus treated is subsequently dipped in a solution to yield the swellable coating, which can be designed according to one of the above-mentioned examples. To remove the air bubbles present in the porous surface 4, this dipping process, once again, preferably takes place in a desiccator to which negative pressure of <200 mbar is applied. After a treatment time between 2 and 5 minutes, the degassing process is completed, and rising air bubbles are no longer visible. The marker surface 4 is wetted with the swellable polymer 3 and removed from the coating solution. If necessary, this is followed by thermally initiated polymerization at >50° C., removal of the solvent in a vacuum drying chamber or direct adhesive bonding in the respective eyelet 2.

After this process, the respective marker is positioned in the appropriate eyelet 2. If necessary, the identical solution to yield the swellable coating, which was used previously to coat the markers 5, was applied to the eyelet environment. After the respective marker 5 has been positioned in the associated eyelet 2, the final thermal treatment is carried out, which results in polymerization of the composite and brings about a sufficient retaining force of the markers 5 in the eyelet 2. Thereafter, once again, the installation of the scaffold 1 in the catheter system takes place.

According to a further example of the invention, a scaffold 1 comprising an X-ray marker 5 made of platinum (Pt) was provided, which includes a macroporous surface 4 roughened by way of micro-peening. This scaffold 1 is, once again, made of a degradable magnesium alloy (see FIG. 4) and has a double eyelet 2 each at the distal end and at the proximal end 102, the eyelet being intended to be filled with X-ray markers 5. The diameter of an eyelet 2 is approximately 350 µm, for example. Round solid markers 5 made of platinum are installed in these eyelets 2. The thickness of these platinum markers 5 is identical to the wall thickness of the scaffold 1 and is, for example, 100 µm. The diameter is approximately 20 µm less than the eyelet diameter. The respective platinum marker 5 was previously roughened by way of micro-peening using corundum particles. The surface roughness thus achieved is between Ra 0.5 µm and Ra 3.0 µm. The surface 4 of the respective marker 5 is thus provided with a microrough porous surface 4. This surface structuring also prompts a considerable enlargement of the real surface by at least a factor of 2. This is an essential prerequisite for the high wettability.

The respective marker 5 thus treated is subsequently dipped in a solution to yield the swellable coating, which is designed according to one of the above examples. So as to remove the air bubbles present in the porous surface 4, this dipping process takes place in a desiccator to which negative pressure of <200 mbar is applied. After a treatment time between 2 and 5 minutes, the degassing process is completed, and rising air bubbles are no longer visible. The marker surface 5 is wetted with the swellable polymer 3 and removed from the coating solution. If necessary, this is followed by thermally initiated polymerization at >50° C., removal of the solvent in a vacuum drying chamber or direct adhesive bonding in the respective eyelet 2.

After this process, the respective marker is positioned in the appropriate eyelet 2. If necessary, the identical solution to yield the swellable coating used previously to coat the markers 5 was applied to the eyelet environment. After the respective marker 5 has been positioned in the associated eyelet 2, the final thermal treatment is carried out, which results in polymerization of the coating of the X-ray marker surface and brings about a sufficient retaining force of the respective marker in the associated eyelet 2. Thereafter, once again, the installation of the scaffold 1 in the catheter system takes place.

According to a further example of the invention, a scaffold 1 comprising an X-ray marker made of an X-ray absorbing metal, such as Pt, Au, W, Ta, or Ir, is proposed, which includes a thin siliceous and thus non-conducting surface 4.

This siliceous surface 4 is achieved by dipping wires made of X-ray marker materials in diluted water glass solutions and subsequent air drying. As a function of the dilution degree of the water glass, electrically insulating layers approximately 1 µm to 10 µm thick form on the wire surfaces. The composition of these layers corresponds to formula $M_2O*nSiO_2$. M can be made of the elements Li, Na or K. The use of Li-containing water glass solutions offers the advantage that the resulting layers have a lower tendency toward cracking after the drying process. Thereafter, the wires thus treated are separated (for example by way of a microtome or a wire saw equipped with microcrystalline diamond bodies) into approximately 100 µm thin sections and further treated as in one of the above-mentioned examples, so as to arrive at a scaffold 1 comprising a coated X-ray marker 5.

The technology of separating by way of the microtome or the diamond wire saw ensures that clean and warp-free cut edges are obtained, and that the silicate layer does not chip. This approach represents both an alternative to the use of swellable polymers and can also be employed in combination with these. This means that the silicate-containing surfaces 4 of the X-ray markers 5 do not develop any corrosion-promoting local element effect even when the adhesive gap includes no, or not sufficient, adhesive.

As a result, the invention advantageously prevents the risk of an inadvertently and suddenly occurring formation of local elements during the clinically relevant support period of the scaffold, and the unpredictable corrosion resulting therefrom, along with intensified local formation of hydrogen and the associated potential undesirable biological reactions in the patient's body.

The invention claimed is:

1. A medical implant, comprising:
a scaffold comprising at least one receptacle for an X-ray marker, the scaffold comprising a first metal;
at least one X-ray marker disposed in the receptacle, the X-ray marker comprising a second metal; and
an electrically insulating coating applied to the X-ray marker that prevents corrosion-promoting contact between the X-ray marker and the scaffold, wherein the X-ray marker has a porous surface, a pore diameter of the surface being in the range of 0.5 micrometers to 3 micrometers and wherein the coating extends into pores of the porous surface and is configured and arranged to emerge from the pores upon contact with a medium containing water, to thereby maintain centering of the X-ray marker in the receptacle.

2. The medical implant according to claim 1, wherein the X-ray marker has a rough surface with a surface roughness value Ra in the range of 0.5 micrometers to 3 micrometers.

3. The medical implant according to claim 1, wherein the coating comprises a superabsorbent polymer selected from the group consisting of polyacrylic acid (PAA), polyglycolic acid (PGA), polyethylene glycol (PEG), and hyaluronic acid (HA), and an adhesive substitute selected from the group consisting of polyureas, polyurethanes, water glass, cyanoacrylate, and a chloroform-containing paraffin solution.

4. The medical implant according to claim 1, wherein the at least one X-ray marker is monolithic.

5. A medical implant, comprising:
a scaffold comprising at least one receptacle for an X-ray marker, the scaffold comprising a first metal;
at least one X-ray marker disposed in the receptacle, the X-ray marker comprising a second metal; and
an electrically insulating coating applied to the X-ray marker that prevents corrosion-promoting contact between the X-ray marker and the scaffold wherein the coating comprises a swellable coating formed of a polymer that undergoes an increase in volume upon contact with a medium containing water, wherein the polymer is a swellable, insoluble, cross-linked polymer.

6. The medical implant according to claim 5, wherein the swellable coating comprises a swellable hydrogel or superabsorbent polymer.

7. The medical implant according to claim 1, wherein the X-ray marker is adhesively attached in the receptacle.

8. The medical implant according to claim 1, wherein the second metal is selected from the group consisting of: tungsten, tantalum, gold, platinum, and iridium.

9. The medical implant according to claim 1, wherein the scaffold is formed of a degradable material.

10. The medical implant according to claim 1, wherein the first metal is magnesium, and the scaffold is formed of a magnesium alloy.

11. A medical implant, comprising:
a scaffold comprising at least one receptacle for an X-ray marker, the scaffold comprising a first metal;
at least one X-ray marker disposed in the receptacle, the X-ray marker comprising a second metal; and
an electrically insulating coating applied to the X-ray marker that prevents corrosion-promoting contact between the X-ray marker and the scaffold, wherein the X-ray marker has a rough surface with a surface roughness value Ra in the range of 0.5 micrometers to 3 micrometers and wherein the coating extends into the rough surface and is configured and arranged to emerge from the surface roughness upon contact with a medium containing water, to thereby maintain centering of the X-ray marker in the receptacle.

12. The medical implant according to claim 11, wherein the X-ray marker is adhesively attached in the receptacle.

13. The medical implant according to claim 11, wherein the second metal is selected from the group consisting of: tungsten, tantalum, gold, platinum, and iridium.

14. The medical implant according to claim 11, wherein the scaffold is formed of a degradable material.

15. The medical implant according to claim 11, wherein the first metal is magnesium, and the scaffold is formed of a magnesium alloy.

16. The medical implant according to claim 6, wherein the coating is a superabsorbent polymer selected from the group consisting of polyacrylic acid (PAA), polyglycolic acid (PGA), polyethylene glycol (PEG), and hyaluronic acid (HA).

17. A method for producing a medical implant, providing a scaffold comprising at least one receptacle for an X-ray marker, the scaffold comprising a first metal, providing an X-ray marker comprising a second metal, applying an electrically insulating coating to the X-Ray marker to form a coated X-Ray marker, and adhesively attaching the coated X-ray marker in the at least one receptacle, wherein the coating solution comprises a hydrogel monomer, a cross-linking agent, a polymerization initiator and a polymerization catalyst.

18. The method according to claim 17, wherein the coating solution is an adhesive for said adhesively attaching.

\* \* \* \* \*